US00PP30434P3

(12) United States Plant Patent
Alfred et al.

(10) Patent No.: US PP30,434 P3
(45) Date of Patent: Apr. 23, 2019

(54) ***CANNABIS* PLANT NAMED 'LW-BB1'**

(50) Latin Name: ***Cannabis indica* L.**
Varietal Denomination: LW-BB1

(71) Applicant: Green Brands, LLC, Denver, CO (US)

(72) Inventors: Andrew Alfred, Denver, CO (US); Ian Dumpert, Denver, CO (US); Kasey Greenwald, Evergreen, CO (US); Christopher Chapdelaine, Denver, CO (US)

(73) Assignee: Green Brands, LLC, Denver, CO (US)

( * ) Notice: Subject to any disclaimer, the term of this patent is extended or adjusted under 35 U.S.C. 154(b) by 0 days.

(21) Appl. No.: 15/731,501

(22) Filed: Jun. 21, 2017

(65) Prior Publication Data

US 2018/0376644 P1 Dec. 27, 2018

(51) Int. Cl.
*A01H 5/00* (2018.01)
*A01H 6/28* (2018.01)

(52) U.S. Cl.
USPC ..... Plt./263.1
CPC ..... *A01H 6/28* (2018.05)

(58) Field of Classification Search
USPC ..... Plt./263.1
See application file for complete search history.

(56) References Cited

PUBLICATIONS

The *Cannabis* encyclopedia Jorge Cervantes. Chapter 2 Measuring Cannabinoids. p. 23-32. 2015.*

* cited by examiner

*Primary Examiner* — Annette H Para
(74) *Attorney, Agent, or Firm* — Stefan J. Kirchanski; Matthew J. Spark; Zuber Lawler & Del Duca LLP

(57) ABSTRACT

'LW-BB1' is a high yielding female *Cannabis* cultivar. The plant shows strongly apically dominant vertical branches, vigorous growth and dark green foliage. The cultivar is very resistant to fungal diseases showing particular resistance to powdery mildew. The inflorescences, which are compact and almost round, are densely covered by glandular trichomes as are the subtending, densely packed foliar bracts. The stems and petioles show purplish markings and the entire inflorescence takes on a somewhat purple cast at maturity. The dried inflorescence shows a richness of terpenoids including β-Myrcene, α-Pinene, Terpinolene and β-Caryophyllene.

6 Drawing Sheets

Genus and species: *Cannabis indica* L.
Varietal denomination: 'LW-BB1'.

CROSS-REFERENCE TO RELATED APPLICATIONS

Not Applicable

U.S. GOVERNMENT SUPPORT

Not Applicable

BACKGROUND OF THE INVENTION

The present invention comprises a new and distinct cultivar of *Cannabis*, botanically known as *Cannabis indica*, and hereinafter referred to by the cultivar name 'LW-BB1.'

'LW-BB1' is the product of a planned breeding program intended to combine some of the most desirable characteristics of two traditionally available varieties. There is considerable botanical controversy surrounding the number of species that are members of the genus *Cannabis*. Although there is strong taxonomic support for treating all *Cannabis* varieties as members of a single, heterogeneous species (*C. sativa*), there is also some precedent for dividing the larger stature varieties that have been selected for fiber production from the somewhat smaller varieties that have been selected primarily for their herbal and medicinal qualities. Under this rubric, the fiber varieties are denominated *C. sativa* and the herbal varieties are denominated *C. indica*. Traditional morphological descriptions find that "*sativa*" varieties are tall with long internodes, long time to maturity and have thin/narrow leaflets; whereas "*indica*" varieties are short, bushy plants with short time to maturity (more responsive to short day conditions) and have wide/broad leaflets. *Cannabis* varieties are often indicated as being either "*sativa*" or "*indica*" as shorthand for the above-described characteristics. The precise genetic provenance of the many *Cannabis* cultivars currently in existence is largely unknown, and all varieties appear to be interfertile so that this shorthand does not denote species, subspecies or any taxonomic rank at all. The parents of 'LL-BB1' are considered to be "*indica*" varieties.

Chemotaxonomy further confounds the nomenclatural debate. Academically, many authors refer to "*sativa*" varieties as being CBD-A (cannabidiolic acid) dominant, with minimal, low levels of THC-A (tetrahydrocannabinolic acid); with the opposite being the case for "*indica*" varieties. Colloquially, however, both types are considered to be THC-A dominant but differ in their psychoactive properties with "*sativa*" varieties being uplifting and energizing, whereas "*indica*" varieties are relaxing and sedating. It has been claimed that the difference in psychoactive properties are caused by the "Entourage Effect" that emerges from the pharmacodynamics of the biologically active secondary metabolites, such as cannabinoids and terpenes, present in the mature inflorescence. In addition, certain organoleptic properties and other traits have been ascribed to herbal *Cannabis* plants having either "*sativa*" or "*indica*" characteristics.

'LW-BB1' is a clone selected from an open-cross of traditional varieties 'DJ Short's Blueberry' and 'Black Berry Kush' that was made in Colorado in 2013. 'DJ Short's Blueberry' is a well-known "*indica*" variety that was purportedly bred in Oregon in the 1970s. The cultivar is a short (3-5 feet) and bushy plant that exhibits heavy lateral branching and short internodes. The female inflorescence typically shows hues of red, purple, deep green, and violet blue while the dried inflorescence also shows violet hues and exhibits a fruity and "skunky" aroma, that is redolent of berries. 'Black Berry Kush' is another "*indica*" variety with medium height (4-7 feet) that is more sparsely branched than 'DJ Short's Blueberry' and has considerably longer internodes. 'Black Berry Kush' plants and flowers are known to show multiple hues of green and sometimes develop purple hues if exposed to cold (temperatures less than 50° F.). 'Black Berry Kush' plants exhibit only shades of mid to deep green when cultivated under artificial light. 'Black Berry Kush' has a very skunky, earthy aroma; the live plant may also have a very subtle aroma of berry, but that aroma does not carry through to the dried herbal product. Some clones of 'Black Berry Kush' are known to be resistant to mold, mildew and other microbial pathogens. 'Black Berry Kush' is a very heavy resin producer, and 'Black Berry Kush' inflorescences have very dense trichome coverage. Neither of these parent varieties are the subjects of plant patents.

The parental cross was made prior to February 2014, and the seeds were planted by the inventors in March of 2014. From the germinated seedlings a phenotypically elite cultivar was identified and reproduced by cuttings to allow test growth. A meristematic tissue culture of one of the cuttings was established on Jun. 23, 2016; plantlets were regenerated from the tissue culture on Sep. 7, 2016. One of the regenerated plantlets showed pronounced vigor and was selected and named 'LW-BB1.' This plant was transferred to the production department in Denver, Colo. on Oct. 11, 2016 and has been asexually reproduced by cutting since that time.

For asexual reproduction, axillary branches of at least three nodes in length were excised from the mother plant. The cuttings were treated with a proprietary gel containing nutrients and auxin and were inserted into one inch cubes of rockwool, recycled organic material or similar rooting media. The cuttings were allowed to root over a period of three weeks at a temperature of 70-80° F., relative humidity of 60-70% and constant illumination at an intensity of 40-100 PPFD (photosynthetic photon flux density as measured in $\mu mol/m^2/s$). Subsequent asexual reproduction by cutting following the above-described method has demonstrated that the new cultivar stably retains the characteristics disclosed below and reproduces true to type through successive generations of asexual reproduction. It is not unusual for *Cannabis* cultivars to lose vigor after successive generations of asexual reproduction by cutting. Vigor is often regained by passage through tissue culture, but vigor is then usually lost again. 'LW-BB1' is unusual in that vigor has thus far been retained through several generations of asexual reproduction by cutting.

BRIEF DESCRIPTION OF THE PHOTOGRAPHS

Figure 1:
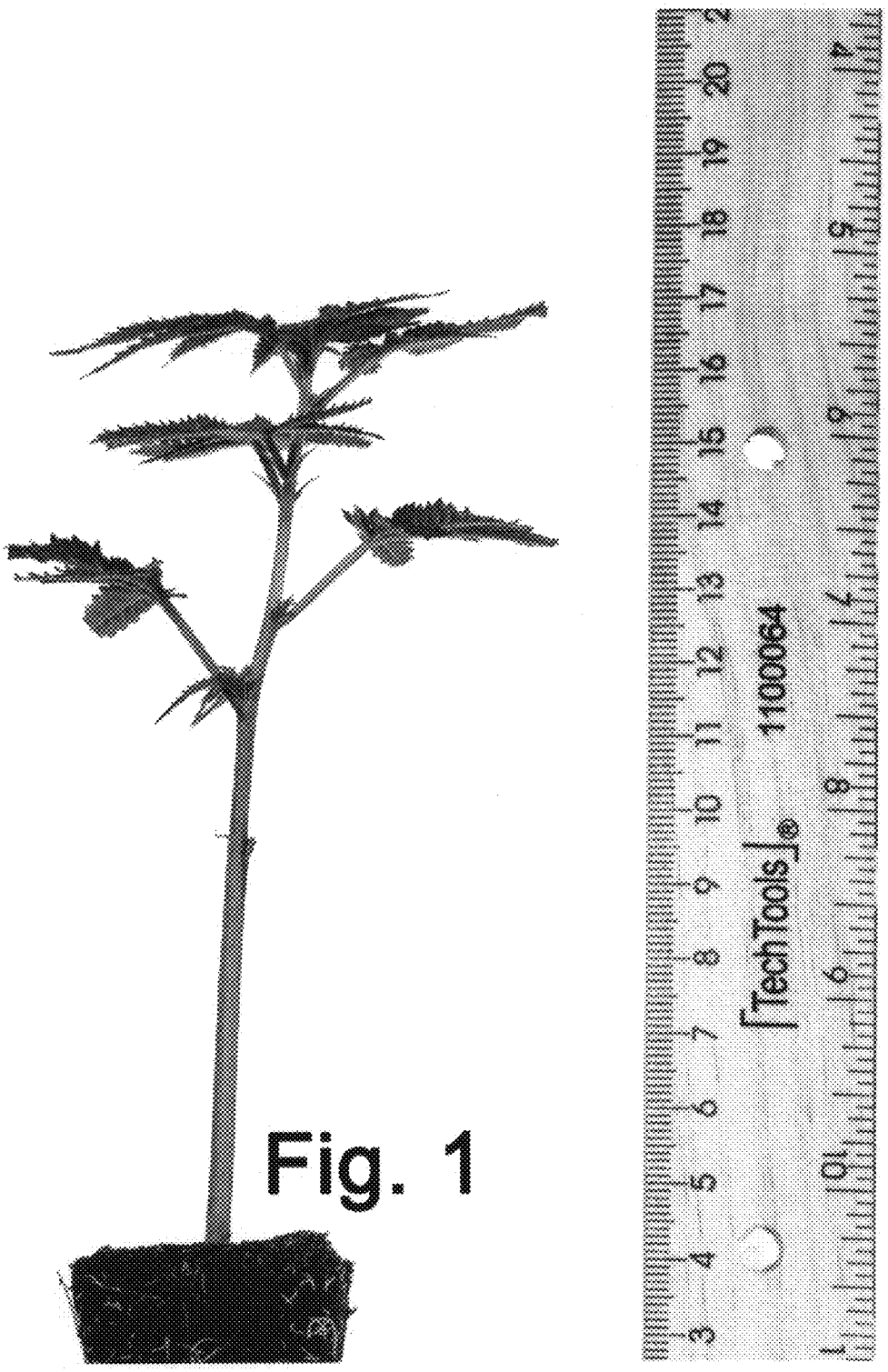
FIG. 1 is a photograph of a 23 day old rooted cutting.
Figure 2:
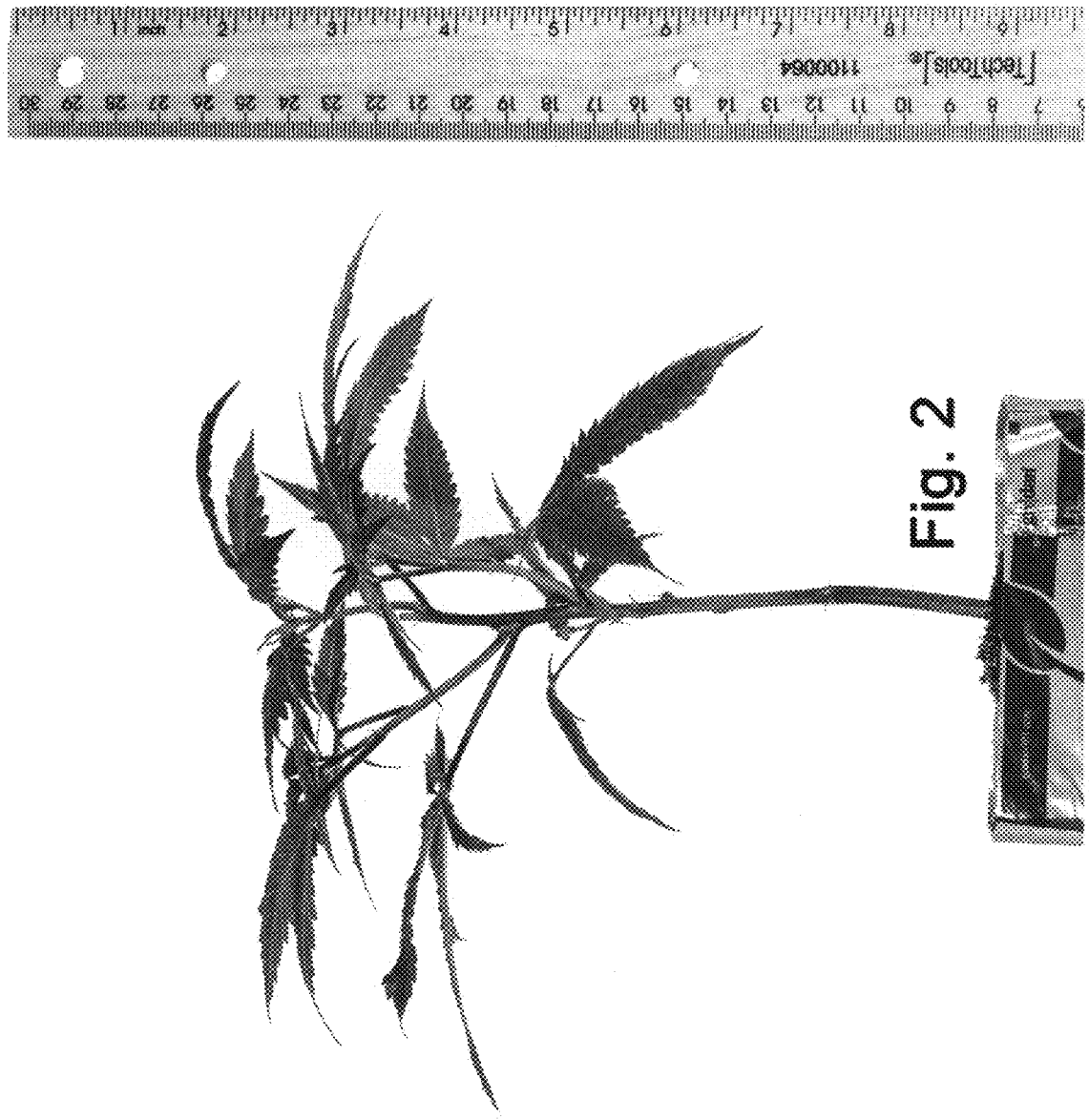
FIG. 2 is a photograph of a 42 day old vegetative plant.
Figure 3:
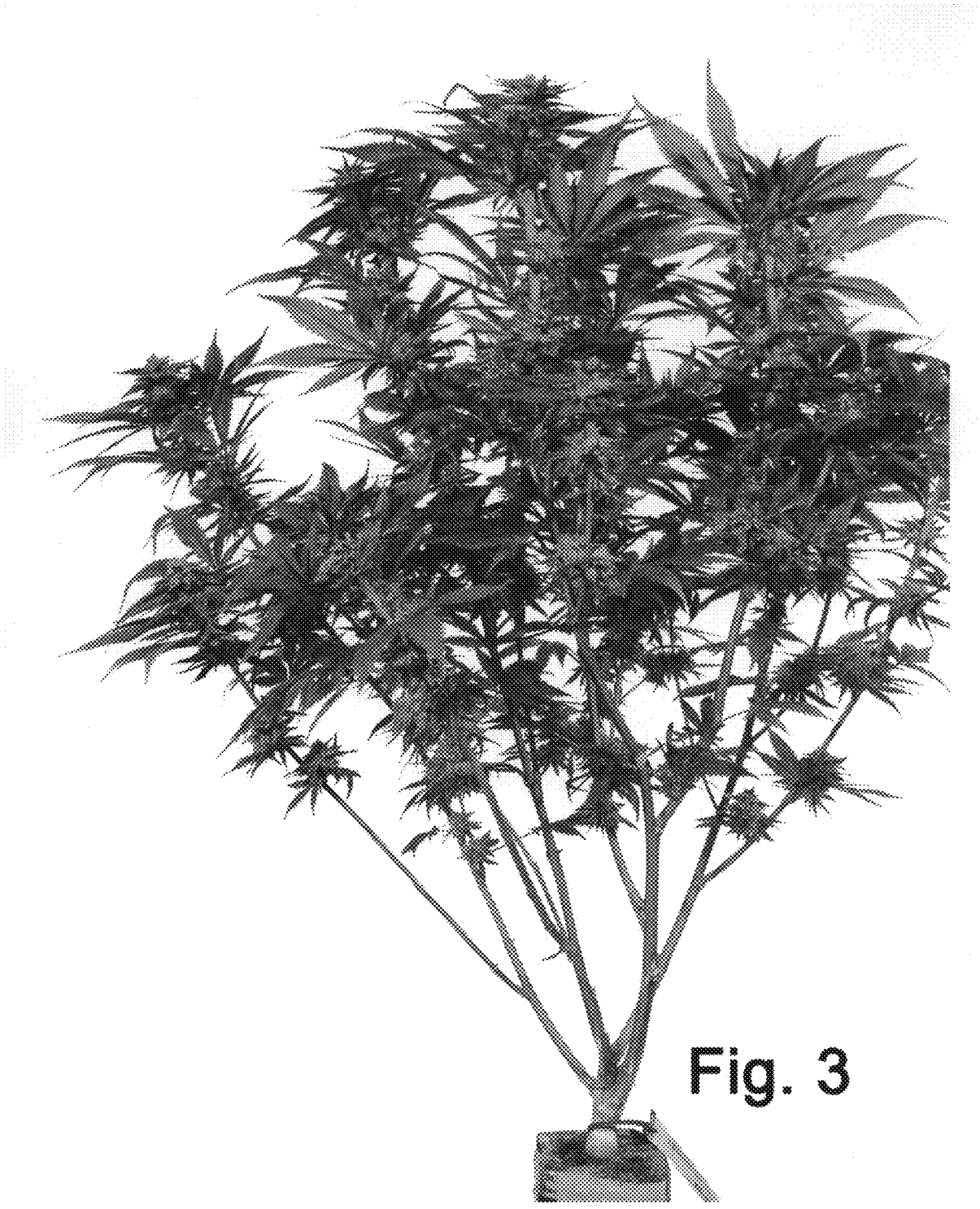
FIG. 3 is a photograph of a 99 day old mature flowering plant that has had its large vegetative leaves and lower branches pruned off.
Figures 4, 5, 6, 7, 8, 9, 10, 11, 12:
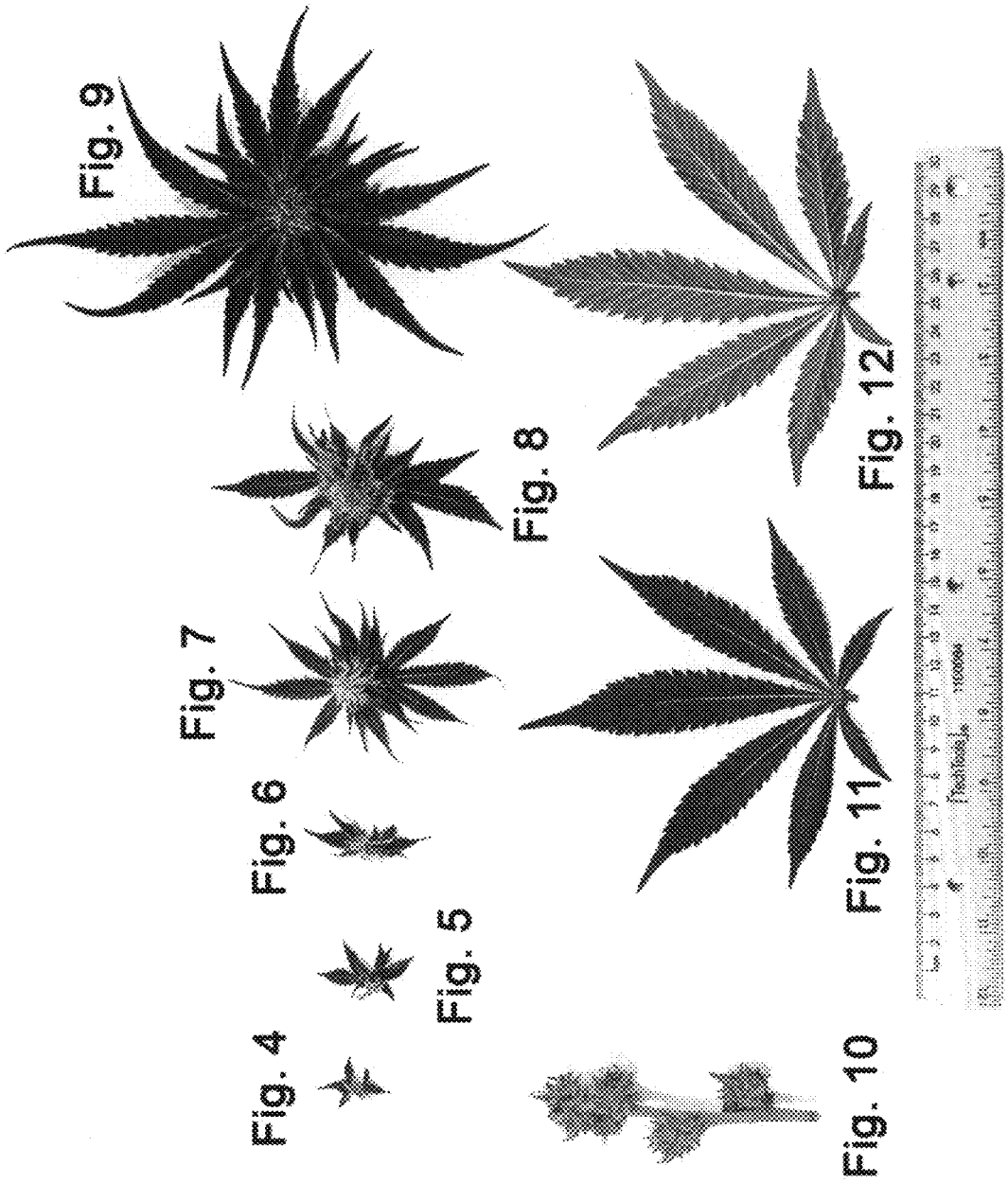
FIG. 4 is a photograph of a small lateral (axillary) female inflorescence at an early stage of stigma elongation also showing the subtending "water" leaf and bract.
FIG. 5 is a photograph of a lateral (axillary) female inflorescence at an early stage of stigma elongation showing an early stage of trichome development and also showing subtending "water leaves" and bracts.
FIG. 6 is a photograph of a lateral (axillary) female inflorescence at a mid-stage of stigma development showing an early stage of trichome development and also showing subtending "water leaves" and bracts.
FIG. 7 is a photograph of a terminal (apical) female inflorescence at a late stage of stigma development showing a mid-stage of trichome development and also showing numerous subtending "water leaves" and bracts.
FIG. 8 is a photograph of a terminal (apical) female inflorescence at a mid-stage of stigma senescence showing a late stage of trichome development and an early stage of floral bract elongation.
FIG. 9 is a photograph of a mature, ready to harvest, terminal (apical) female inflorescence showing stigma senescence, fully elongated floral bracts, fully developed trichomes and overall anthocyanin production.
FIG. 10 is a photograph of the top portion of a mature flowering stem with leaves removed to show attachment of the terminal inflorescence.
FIG. 11 is a photograph of the upper surface of a mature vegetative leaf having seven leaflets.
FIG. 12 is a photograph of the lower surface of a mature vegetative leaf having seven leaflets.
Figures 13, 14, 15, 16, 17, 18, 19, 20, 21, 22, 23:
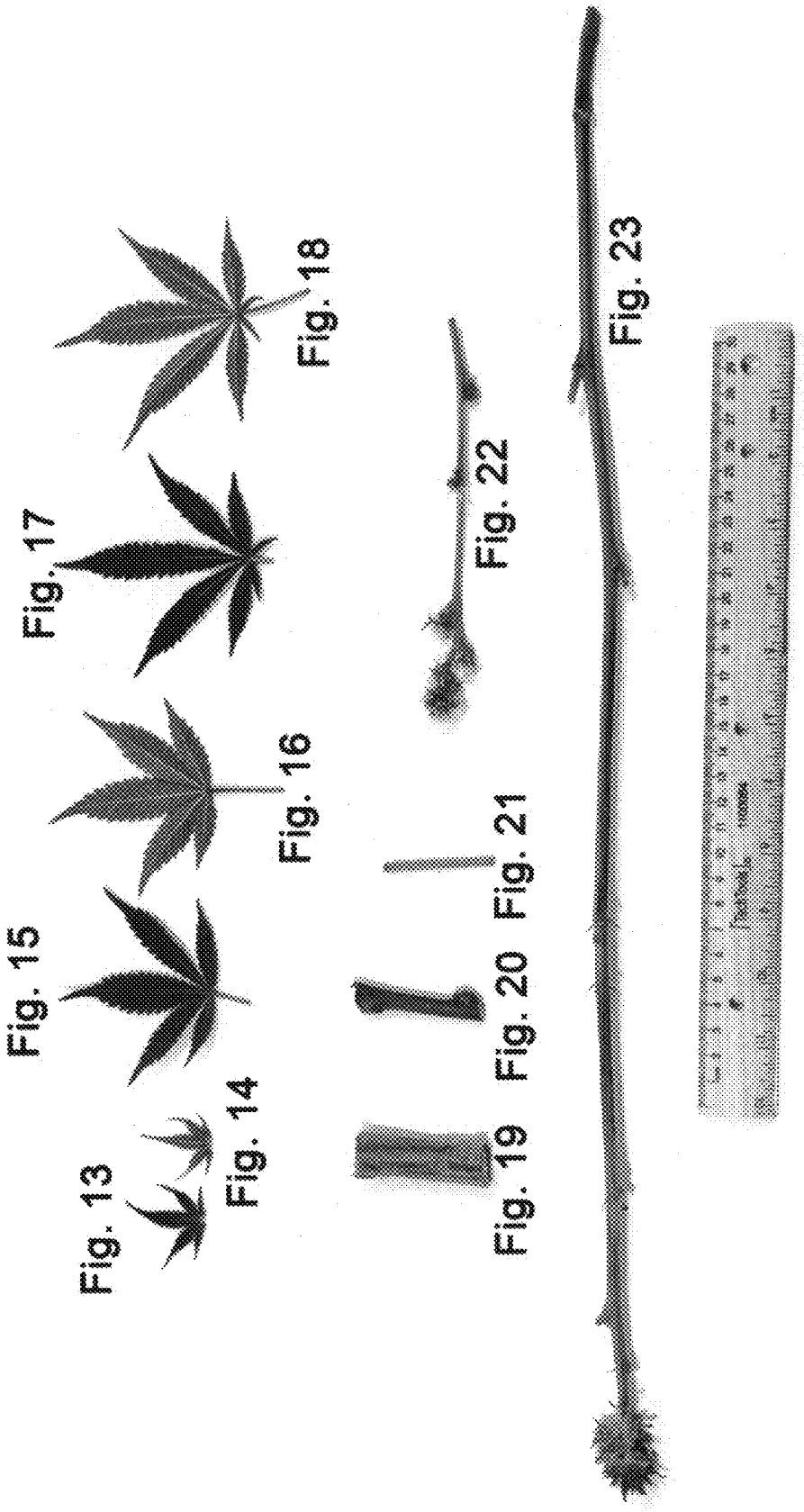
FIG. 13 is a photograph of a "water leaf" from an inflorescence showing the upper surface of a small leaf having five leaflets.
FIG. 14 is a photograph of a "water leaf" from an inflorescence showing the lower surface of a small leaf having five leaflets
FIG. 15 is a photograph of a leaf from a mature flowering plant showing the upper surface and petiole of a young vegetative leaf having five leaflets.
FIG. 16 is a photograph of a leaf from a mature flowering plant showing the lower surface and petiole of a young vegetative leaf having five leaflets.
FIG. 17 is a photograph of a leaf from a mature flowering plant showing the upper surface and petiole of a young vegetative leaf having seven leaflets.
FIG. 18 is a photograph of a leaf from a mature flowering plant showing the lower surface and petiole of a young vegetative leaf having seven leaflets.
FIG. 19 is a photograph of a portion of the lower part of a mature stem showing the development of corky lenticels and exfoliation of the original epidermis.
FIG. 20 is a photograph of an internode with two nodes from the middle portion of a mature stem showing characteristic anthocyanin markings.
FIG. 21 is a photograph of a young internodal stem segment from near the apex.
FIG. 22 is a photograph of a flowering stem showing both lateral and terminal inflorescence attachment.
FIG. 23 is a photograph of a flowering stem with leaves removed to show terminal inflorescence attachment as well as internodal spacing and stipules.
Figure 24:
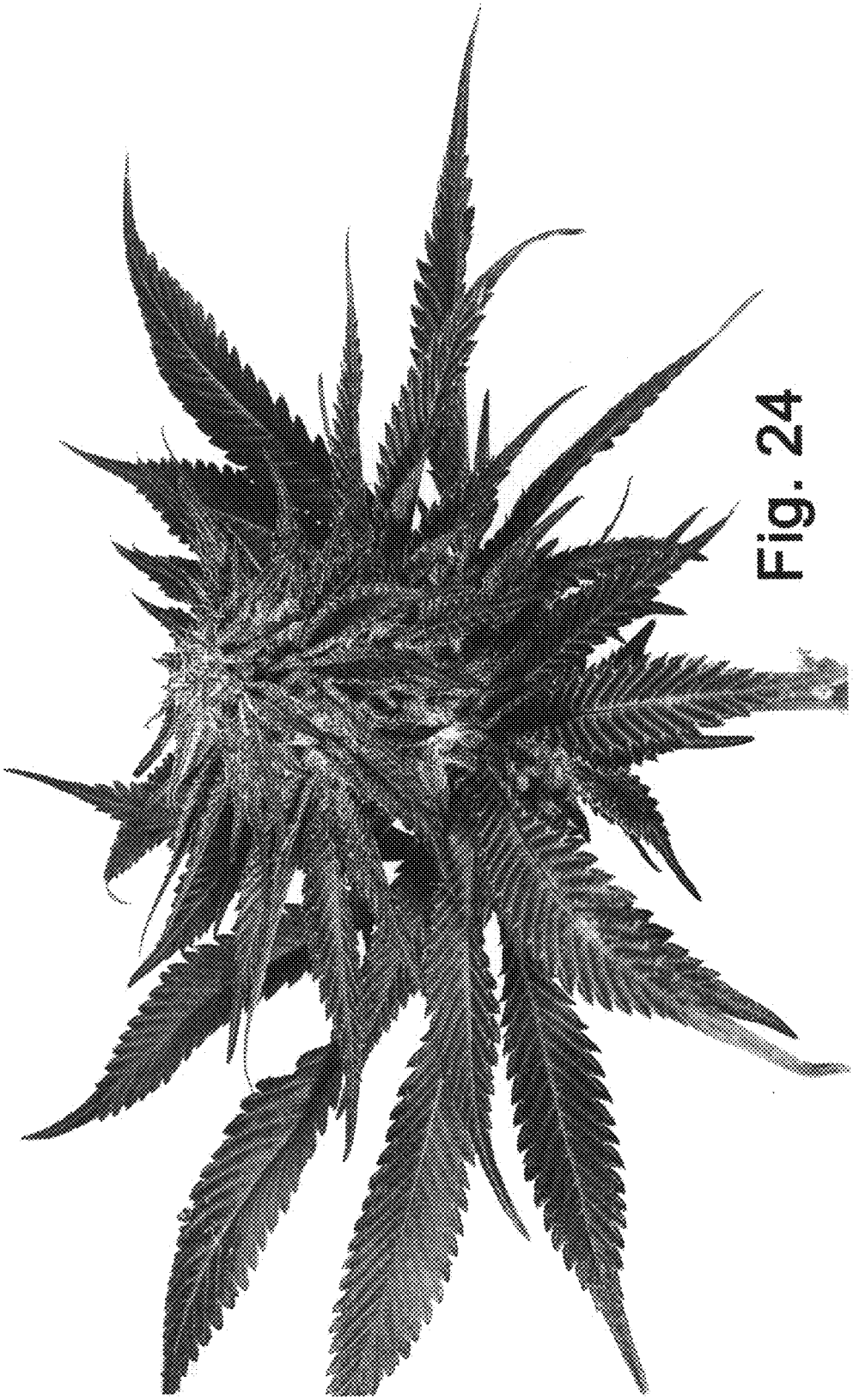
FIG. 24 is a photograph of a mature apical inflorescence showing the typical red-purple cast of the "water leaves" and floral bracts.

The colors of these photographic illustrations are as nearly true as is possible with color illustrations of this type but may vary with lighting conditions and, therefore, the color characteristics of this new cultivar should be determined with reference to the observations reported herein according to Royal Horticultural Society Colour Chart, Sixth Edition (2015), rather than from these illustrations alone.

DETAILED BOTANICAL DESCRIPTION

The following description is based on observations made in Spring of 2017 on plants produced according to an ordinary growth cycle as described below. However, the present invention has not been evaluated under all possible environmental conditions; therefore, the phenotype may vary with alterations in the growth environment without a change in the genotype of the plant.

Following rooting, the cuttings were transplanted into either four or six inch rockwool blocks. Plants in four inch blocks were grown for approximately three-four weeks or until roots emerged from the bottoms of the blocks. Then, they were placed on top of six inch rockwool blocks as the final growth media. Plants were then grown for an additional three-four week period. During growth, all plants were fed and watered with a dilute solution of water soluble fertilizer dispensed through emitters placed on top of the rockwool blocks. Carbon dioxide concentration was measured and supplemented as required. Vegetative growth was at a temperature of 70-80° F. and relative humidity of 50-65% with constant illumination of 100-300 PPFD provided by either Red/Blue LED, broad spectrum LED, 3200K Fluorescent, HID Metal Halide or mixtures thereof.

After adequate vegetative growth had been attained, flowering was induced by altering the photoperiod to 12 hour days (i.e., 12 hours light-12 hours dark). Light intensity was increased to 400-1000 PPFD; other growth conditions were maintained as already described. The plants were mature and ready to harvest between 6-8 weeks after flowering was induced. Maturity was determined using trichome and stigma color, floral bract development and vegetative leaf senescence as cues.

'LW-BB1' shows strong apical dominance and does not branch outwards like its 'Blueberry' parent. Once pruned, the branches grow vertically upwards. The spacing between inflorescences is different than either of its parents. The overall inflorescence (AKA "bud") of 'LW-BB1' is compact and almost round; both of 'LW-BB1's' parents have more elongate, spear shaped inflorescences.

'LW-BB1' cultivar is very resistant to diseases such as mold and mildew; its resistance to powdery mildew is quite remarkable allowing culture with virtually no use of fungicides.

Trichome coverage in 'LW-BB1' inflorescences is very impressive and exceeds that of most other cultivars. The aroma and flavor of 'LW-BB1' is also unique. It has a dank, earthy, almost woody smell (like a forest floor) that is accentuated by a subtle berry sweetness—a combination found in neither of its parents. The smells or flavors are described as "skunk," "pine," berry," "earthy," "woody" as well as "kush," "hash" and "Afghani" which are terms used to describe a hashish-like odor which has also been described as "complex, rich, dank, and earthy—the way fresh tilled-soil smells, [plus] musty, piney, and woody combined with a touch of fossil fuel-like gassiness and a subtle underlying sweetness."

'LW-BB1' shows quite vigorous growth during its vegetative state. The inventors have recorded a range of 0.7 to 1.07 inches of growth per day for 'LW-BB1', which measurement includes multiple pruning events. (The average growth recorded for all other cultivars measured is 0.66 inches per day under identical growth conditions.)

As a vegetative *Cannabis* plant grows both leaf size and leaflet number increases. 'LW-BB1' generally has between five and seven leaflets. The vegetative leaves have petioles and both the stems and petioles show surface anthocyanin coloring (RHS 186C); the petioles of immature leaves are often uniformly colored (RHS 142D) while the stems are green (RHS 131D) with anthocyanin streaking (RHS N79B). The petiolate vegetative leaves are dark green (RHS 131C) on their adaxial (upper) surfaces and somewhat lighter green (RHS 136D) on the abaxial (lower surfaces). Colloquially the vegetative leaves are known as "fan leaves."

During the first two-three weeks following the start of floral induction, existing internodes undergo a process of accelerated elongation. This is called "stretching" in the art of *Cannabis* culture, and the degree of "stretching" is both cultivar dependent, varying from cultivar to cultivar, and environmentally dependent, varying according to the growth conditions. Generally, the plant increases from 50% to 100% in height. Under the growing conditions described herein, 'LW-BB1' stretches 71% ±13%. After the "stretching" period, internodal elongation of new internodes is reduced resulting in somewhat bunched leaves or bracts that are reduced in size as compared to vegetative leaves. The leaves/bracts in the flowering portion of the stem are smaller having a reduced number of leaflets and shortened (or nearly absent) petioles. These reduced leaves are colloquially known as "water leaves" when they have multiple leaflets.

The inflorescence of 'LW-BB1', like that of virtually all *Cannabis* cultivars, is a compound raceme with greatly shortened internodes. The apical region of the inflorescence normally has bracts with a single lanceolate blade (i.e., not "water leaves"). The initial bracts (i.e., lower) usually have serrate margins like a foliage leaflet, but ultimately bracts with smooth, entire margins are initiated. Compared to floral bracts in many other plants, the floral bracts of *Cannabis* are unusually large and may closely resemble a single leaflet of a vegetative leaf. In a *Cannabis* inflorescence two small pistillate flowers arise in the axil of each bract and are largely hidden in the bunched bouquet of foliar bracts and leaves. Each *Cannabis* flower is wrapped by an involucral bracteole (which may developmentally represent a pair of fused involucral bracteoles), and this structure is colloquially known as the "calyx." Each flower bears two elongate stigmas that are exerted beyond the floral bracts. The receptive surfaces of the stigmas bear numerous straight non-cystolithic trichomes, and the stigmas of 'LW-BB1' range from light greenish to yellowish white (RHS 155A) while growing and while receptive. They darken to orange/orange-yellow (RHS 24B) and then brownish (RHS 164B) as they senesce. The floral bracts of 'LW-BB1' are densely covered with capitate glandular trichomes giving them a sparkling appearance. Following anthesis, as the stigmas senesce, the involucral bracteole/bracteoles ("calyx") of 'LW-BB1' elongate and take on a purplish cast (RHS 186C) particularly at their tips. The bracts/leaves subtending the inflorescence may also exhibit a purplish cast (ranging from RHS 186C to RHS N186C on the upper surfaces and RHS 186C to RHS N77B on the lower surfaces).

As can be gathered from the photographs, lateral inflorescences develop in the axils of many of the vegetative leaves farther down the stem. The same pattern is repeated on most of the lateral branches of the plant: an apical inflorescence as described above with smaller lateral inflorescences in the axils of lower vegetative leaves.

The inflorescences including the subtending bracts and leaves rich in glandular trichomes are harvested and dried as the final herbal product. Under the specified growing conditions, the time to maturity is about 45 days from start of floral induction (i.e. exposure to 12 hour days) and the plants are 90-95 days old at harvest with a final height of 94.55+/−13.43 cm. The time to maturity is highly characteristic of *Cannabis* cultivars and under the described growing conditions can vary from 35 days to 105 days depending on cultivar. 'LW-BB1' has a time to maturity of 45 days.

The following measurements are averages (with standard deviation) of 10 measurements made from 90 days old (from date of taking the cutting) flowering plants grown as described above and heavily pruned for production purposes. 'LW-BB1' is a strictly female clone. No male flowers were observed; foreign pollen was excluded so that no seed set was observed.

Size:

*Height*.—94.55±13.93 cm.

*Width*.—54.72±5.36 cm.

Stem:

*Stem morphology*.—Rugose — longitudinal ribs with corky lenticels on older portions.

*Stem color*.—Young stem, light green (RHS 142D); more mature stem green (RHS 131D) with red/magenta-purple longitudinal streaks and nodal coloration (RHS N79B).

*Stem diameter bottom*.—1.96±0.24 cm.

*Stem diameter top*.—0.58±0.07 cm.

*Maximum internode length*.—10.49±2.70 cm.

*Number of internodes on longest stem*.—17±3.

Foliage:

*Phyllotaxis*.—Alternate.

*Leaves*.—Palmately compound, 5-7 linear-lanceolate leaflets with serrate margins.

*Leaf number*.—Vegetative ("fan") leaves on observed plants: 72±25.

*Length mature leaf blade* (*from insertion of petiole to tip of longest leaflet*).—13.6±2.71 cm.

*Width mature leaf blade*.—14.92±1.89 cm.

*Leaflet width* (*largest leaflet*).—2.98±0.54 cm.

*Leaf color-upper surface*.—Dark green, RHS 131C.

*Leaf color-lower surface*.—Light green, RHS 136D.

*Mature petiole*.—Length: 5.76±1.16 cm; Diameter: 3.66±0.58 mm.

*Petiole color*.—Light green, (RHS 142D); some petioles purplish (RHS 186C) especially at insertion into blade.

*Stipules*.—2, one on either side of insertion of petiole, acuminate.

*Stipules*.—Length: 0.64±0.19 cm; Width: 1.08±0.17 mm.

*Stipule color*.—Whitish to yellowish (RHS NN155A to NN 155B).

Inflorescence:

*Habit*.—The apical inflorescence of 'LW-BB1' is a relatively short, compact, compound raceme subtended by crowded reduced leaves ("water leaves") and/or bracts (the "bouquet") densely covered by capitate, glandular trichomes with the small, pistillate flowers buried in the bracts. The trichomes in 'LW-BB1' are not strongly colored even in a mature inflorescence (RHS NN155B). The main apical inflorescence is duplicated by lateral (axillary) inflorescences lower on the stem. "Water leaves" with 7, 5 and 3 leaflets are observed with the larger number of leaflets towards the base of the inflorescence. The more terminal nodes of the inflorescence are marked by simple bracts. The "water leaves" subtend secondary inflorescence branches which often bear "water leaves" subtending tertiary inflorescence branches. The terminal nodes of all of the inflorescence branches usually bear only bracts each of which subtends a pair of flowers. Thus, the inflorescences of 'LW-BB1' contain a significant number of secondary and some tertiary branches. The degree of secondary and tertiary branching varies significantly from cultivar to cultivar. At maturity of the inflorescence the "bouquet" leaves as well as the floral bracts of 'LW-BB1' take on a purplish cast (RHS N186C) as shown in the figures.

*Number* (*per plant*).—133±31.

*Size* (*apical inflorescence*).—

*Length*.—5.95±1.28 cm.

*Width*.—3.15±0.59 cm.

Flowers:

*Corolla*.—Hyaline petals and/or calyx unified and collectively appressed to and surrounding the ovary so as not to be visible without microscopic dissection; flower enveloped by an involucral bracteole (may developmentally be pair of fused involucral bracteoles), colloquially referred to as "calyx," the elongated tip of which is visible in the mature inflorescence. As the inflorescence matures the "calyx" elongates and develops purplish anthocyanin (RHS 186C) markings.

*Number* (*per apical inflorescence*).—21±5.

*Stigmas*.—Two per flower, tapering distally and heavily covered by short, straight non-cystolithic trichomes.

*Stigma color*.—Whitish-yellow (RHS NN155A) turning orange-yellow (RHS 24B) and drying brownish (RHS 164B).

*Stigma length*.—0.811±0.142 cm.

*Stigma width*.—0.056±0.023 cm.

Chemical constituents: Table I shows the typical Cannabinoid profile of 'LW-BB1' expressed as weight/weight percent ('%') of the dried herbal product. These data were obtained by TEQ Analytical Laboratories of Aurora, Colo. The laboratory is accredited to ISO/IEC standards (ISO 17025) through the American Association of Laboratories Accreditation (the A2LA). Cannabinoid measurements reported herein were performed using High Performance Liquid Chromatography (HPLC) on samples of dried inflorescence (dried herbal material). The cultivar is moderately high in cannabinoids (12-15%). Essentially all of the cannabinoids are present as tetrahydrocannabinolic acid (THCA). THC is technically a product of THCA decarboxylation and is not directly synthesized by the plant. However, it will be appreciated that THCA spontaneously breaks down into THC and that elevated temperatures during the drying of herbal material frequently results in total or near total conversion of THCA into THC. Therefore, it is common to indicate the calculated THC content by calculating the amount of THC that will be produced by decarboxylation of a given weight of THCA by multiplying the THCA weight by 0.877 (which number represents the ratio of the molecular weight of THC to that of THCA) and adding the resulting number to the figure that represents any THC that was detected. Calculated THC represents the total amount of THC that is available in a given sample. Tables II and III present the terpene/terpenoid profile of 'LW-BB1' expressed as weight/weight percent ('%') of the dried herbal product. Terpenes were analyzed using gas chromatography-mass spectrometry (GC-MS). Samples from three separate harvests of 'LW-BB1' were analyzed; sample 2 and 3 are not as recent as sample 1 which might account for some loss of terpenoids. The dried herbal product is 0.64-1.1% weight/weight non-cannabinoid terpenes/terpenoids.

TABLE I (Cannabinoids)

| Sample batch | CBGA | CBG | THCA | THC | THC calculated |
|---|---|---|---|---|---|
| 1 | N/A | N/A | 13.9 | none detected | 12.2 |
| 2 | 0.35 | none detected | 14.8 | 0.19 | 13.2 |
| 3 | 0.229 | none detected | 11.8 | 0.19 | 10.5 |

| Sample batch | CBN | CBDA | CBD | CBC | Total Cannabinoids |
|---|---|---|---|---|---|
| 1 | none detected | none detected | none detected | N/A | 13.90 |
| 2 | none detected | none detected | none detected | none detected | 15.34 |
| 3 | none detected | none detected | none detected | none detected | 12.27 |

("N/A" + "not analyzed")

CBGA (cannabigerolic acid); CBG (cannabigerol); CBN (cannabinol); CBDA (cannabidiolic acid); CBD (cannabidiol); CBC (cannabichromene)

TABLE II (Terpenes/terpenoids)

| Sample batch | terpinolene | linalool | β-myrcene | citronellol | α-pinene | Limonene |
|---|---|---|---|---|---|---|
| 1 | 0.0015 | 0.0202 | 0.6184 | 0.0017 | 0.1617 | 0.0369 |
| 2 | 0.0016 | 0.0177 | 0.3717 | 0.0007 | 0.1430 | 0.0230 |
| 3 | 0.0016 | 0.0143 | 0.3053 | 0.0006 | 0.0826 | 0.0181 |

TABLE II-continued (Terpenes/terpenoids)

| Sample batch | β-calyophyllene | α-humulene | β-pinene | borneol | camphene |
|---|---|---|---|---|---|
| 1 | 0.147700 | non detected | 0.0851 | none detected | 0.0041 |
| 2 | 0.1265 | 0.0304 | 0.0753 | none detected | 0.0033 |
| 3 | 0.1166 | 0.0294 | 0.0468 | none detected | 0.0022 |

TABLE III (Terpenes/terpenoids)

| Sample batch | (-) sabinene | ocimene | α-terpinene | δ-3 carene | L-fenchone |
|---|---|---|---|---|---|
| 1 | none detected | 0.0065 | 0.0005 | 0.0006 | 0.0005 |
| 2 | none detected | 0.0043 | 0.0005 | 0.0006 | 0.0005 |
| 3 | none detected | 0.0035 | 0.0005 | 0.0007 | 0.0004 |

| Sample batch | p-cymene | α-phellandrene | α-terpineol | fenchol | Total Terpenes/terpenoids |
|---|---|---|---|---|---|
| 1 | none detected | 0.0018 | 0.0066 | 0.0074 | 1.10 |
| 2 | none detected | 0.0015 | 0.0059 | 0.0073 | 0.81 |
| 3 | none detected | 0.0016 | 0.0050 | 0.0060 | 0.64 |

'LW-BB1' is characterized by a distinct richness of terpenoids. It typically contains detectable amounts of terpinolene, citronellol, camphene, ocimene, alpha terpinene, δ-3 carene and I-fenchone, compounds that could not be detected in the elite cultivar from which the tissue culture was established on Jun. 23, 2016. Compared to the parents 'LW-BB1' has a higher terpene content (a sample of 'DJ Short's Blueberry' showed a total terpene/terpenoid content of 0.46% while a sample of 'Black Berry Kush' showed a total terpene/terpenoid content of 0.64%) and more β-myrcene and β-pinene (a sample of 'DJ Short's Blueberry' showed a β-myrcene content of 0.56% and a β-pinene content of 0.038% while a sample of 'Black Berry Kush' showed a β-myrcene content of 0.27% and a β-pinene content of 0.032%). 'LW-BB1' has detectable terpinolene, citronellol, α-terpinene, and β-3 carene whereas none of these was detected in the parents. 'LW-BB1' has somewhat lower cannabinoid levels than the parents (13.98%—average of three samples). A sample of 'DJ Short's Blueberry' shows a total cannabinoid content of 25.22% (25.14% THC and 0.08% CBD) while a sample of 'Black Berry Kush' showed a total cannabinoid content of 21.77% (21.71% THC and 0.06% CBD). Both parents have detectable levels of CBD while no CBD was detected in 'LW-BB1.' Because 'LW-BB1' has a higher level of terpene/terpenoids and a lower level of cannabinoids than either of the parents, it is likely that the effect of terpene/terpenoids is more predominant than in either of the parents.

What is claimed is:

1. A new and distinct *Cannabis* plant as shown and described.

* * * * *